(12) United States Patent
Oakes

(10) Patent No.: US 7,651,463 B2
(45) Date of Patent: Jan. 26, 2010

(54) PUMP

(76) Inventor: John Oakes, 49A South Parade, Ossett, West Yorkshire WF5 0EF (GB)

( * ) Notice: Subject to any disclaimer, the term of this patent is extended or adjusted under 35 U.S.C. 154(b) by 0 days.

(21) Appl. No.: 11/661,760

(22) PCT Filed: Sep. 2, 2005

(86) PCT No.: PCT/GB2005/003416

§ 371 (c)(1),
(2), (4) Date: Feb. 5, 2008

(87) PCT Pub. No.: WO2006/024874

PCT Pub. Date: Mar. 9, 2006

(65) Prior Publication Data

US 2008/0269554 A1      Oct. 30, 2008

(30) Foreign Application Priority Data

Sep. 3, 2004      (GB)      ................... 0419557.4

(51) Int. Cl.
*A61F 5/00*      (2006.01)

(52) U.S. Cl. ........................................................ 600/38
(58) Field of Classification Search .............. 600/38–41
See application file for complete search history.

(56) References Cited

U.S. PATENT DOCUMENTS

| 4,753,227 | A | | 6/1988 | Yanuck, Jr. | |
|---|---|---|---|---|---|
| 5,095,895 | A | | 3/1992 | Walsh | |
| 5,421,808 | A | * | 6/1995 | Osbon et al. | ................... 600/38 |
| 5,468,211 | A | | 11/1995 | Welch | |
| 5,647,837 | A | | 7/1997 | McCarty | |
| 5,782,621 | A | * | 7/1998 | Harris | ........................ 417/470 |

FOREIGN PATENT DOCUMENTS

DE            43 25 646            11/1994

* cited by examiner

*Primary Examiner*—John P Lacyk
(74) *Attorney, Agent, or Firm*—Venable LLP; Michael A. Sartori; Steven J. Schwarz

(57) ABSTRACT

A pump (102) comprising a chamber (108) adapted to receive a penis, a non-return valve (156), and pumping means (110) operable to pump fluid from the chamber (108), wherein the pump (102) is adapted for use under water.

25 Claims, 3 Drawing Sheets

PUMP

CROSS-REFERENCE TO RELATED APPLICATIONS

The present application is the U.S. National Stage of International Application No. PCT/GB2005/003416, filed in the United Kingdom on Sep. 2, 2005, which claims priority from United Kingdom Application No. GB 0419557.4, filed on Sep. 3, 2004.

BACKGROUND OF THE INVENTION (i) Field of the Invention

The present invention relates to a pump, particularly although not exclusively to a pump for causing or enhancing an erection of a penis particularly, a human penis.

(ii) Description of Related Art

Erection pumps have been known in the art for some years. The manner in which such pumps work is by placing a chamber over a flaccid penis and evacuating the chamber. The evacuation causes a pressure differential between the inside and outside of the chamber. The lower pressure within the chamber causes blood to flow into the penis and thus make the penis erect.

Many pumps known in the art comprise a chamber having a diaphragm at a lower end thereof and a tube attached at an upper end thereof. The tube is connected to a hand held pump device which is usually in the form of an inflatable bulb having a non-return valve therein. In use, a user places the penis through the diaphragm into the chamber and removes air from the chamber by use of the pump.

Problems with conventional pumps are that the erection produced using such pumps is not very long lived and not of adequate erectness.

BRIEF SUMMARY

It is one aim of embodiments of the present invention to address the above mentioned problems and provide a solution which induces a strong erection which is long lived.

According to a first aspect of the present invention there is provided a pump comprising a chamber adapted to receive a penis, a non-return valve, and pumping means operable to pump fluid from the chamber, wherein the pump is adapted for use under water.

Preferably, the chamber is adapted to receive a human penis.

Preferably, the chamber is substantially circular in section. Preferably, the chamber is transparent.

Preferably, the chamber comprises a neck section toward a second end thereof, which preferably comprises an outlet.

Preferably, the pump comprises a cap section within which is preferably accommodated the non-return valve. Preferably, the cap section is adapted to fit over the neck section and form a fluid tight seal therewith.

Preferably, the pump is a penis pump. By penis pump it is meant a pump adapted to cause or enhance an erection to a human penis.

By non-return valve it is meant a valve which allows fluid to travel through the valve in one direction, but not in the other. Preferably, the non return valve is adapted to allow the expulsion of fluid from the chamber, but not the ingress of fluid into the chamber.

Preferably, an exterior portion of the neck section is threaded. Preferably, an interior portion of the cap section is threaded. Preferably, the threaded portion of the neck section is adapted to threadedly engage with the threaded portion of the cap section. Preferably, sealing means are provided between the cap section and the neck section which sealing means is preferably an O-ring.

Preferably, the cap section is adapted to be screwed onto the neck section.

Preferably, the pumping means is situated toward a first end of the chamber. Preferably, the pumping means is manually actuated. Preferably, the pumping means extends from a first end of the chamber. Preferably, the pumping means is coaxial with the chamber. Preferably, the pumping means comprises a compressible gaiter. Preferably, the pumping means comprises a resilient bias operable to return the pumping means to an uncompressed configuration.

Preferably, the pump comprises sealing means operable to seal the pump onto the body of a user. Preferably, the sealing means is situated at the first end of the pump. Preferably, the sealing means comprises a sealing ring which is preferably made from closed cell rubber sponge or similar.

Preferably, the sealing means comprises a cutaway section on a face thereof which seals against the body of a user, when in use. Preferably, the sealing means comprises a ring having a cutaway section therefrom.

Preferably, the sealing means comprises a sealing ring having a chamfer along a section of an underside thereof.

Preferably, the pump comprises pressure release means which is preferably situated toward the neck section of the chamber. Preferably, the pressure release means comprises a plug which is accommodated in an aperture in a wall of the chamber. Preferably, the pressure release means is operable to be moved between a first position in which it does not allow fluid to flow between an interior and an exterior of the chamber and a second position in which it does allow fluid to flow between an interior and an exterior of the chamber, preferably by application of pressure by a user.

Preferably, the pressure release means is situated at a position on the chamber which is generally radially opposite the cutaway section of the sealing means but, preferably, longitudinally displaced therefrom.

Preferably, the pumping means further comprises a gas filled chamber which is preferably annular in shape. Preferably, the gas filled chamber is attached to an inner face of the sealing ring. Preferably, the gas filled chamber is operable to be compressed by the application of pressure by a user. Preferably, a spring return force of the gas filled chamber is greater than the resilient bias of the gaiter.

Preferably, between the gaiter and the hollow chamber is a fixing ring. Preferably, the fixing ring is formed of polycarbonate. Preferably, the fixing ring is adapted to provide lateral and reciprocal support.

According to a second aspect of the present invention there is provided a method of causing or enhancing an erection of a human penis comprising immersing a pump as defined by the first aspect in water, placing a flaccid penis into a chamber of the pump and using pumping means to pump water from the chamber through a non-return valve.

BRIEF DESCRIPTION OF THE DRAWINGS

All of the above aspects may be combined with any feature described herein and in any combination.

For a better understanding of the invention, and to show how embodiments of the same may be carried into effect, reference will now be made, by way of example, to the accompanying diagrammatic drawings in which.

DETAILED DESCRIPTION

Figure 1:
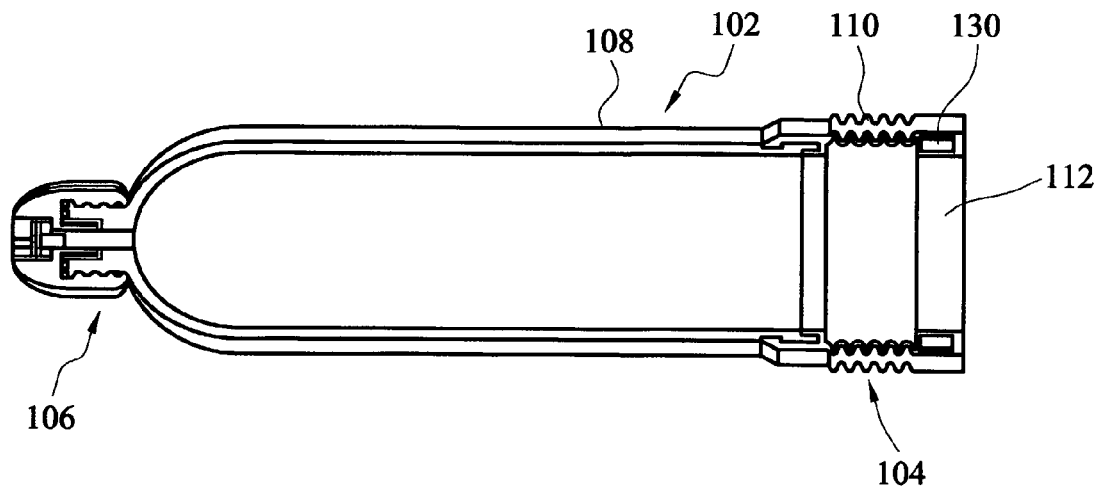
FIG. 1 shows a sectional view of a pump in an uncompressed configuration.
Figure 2:
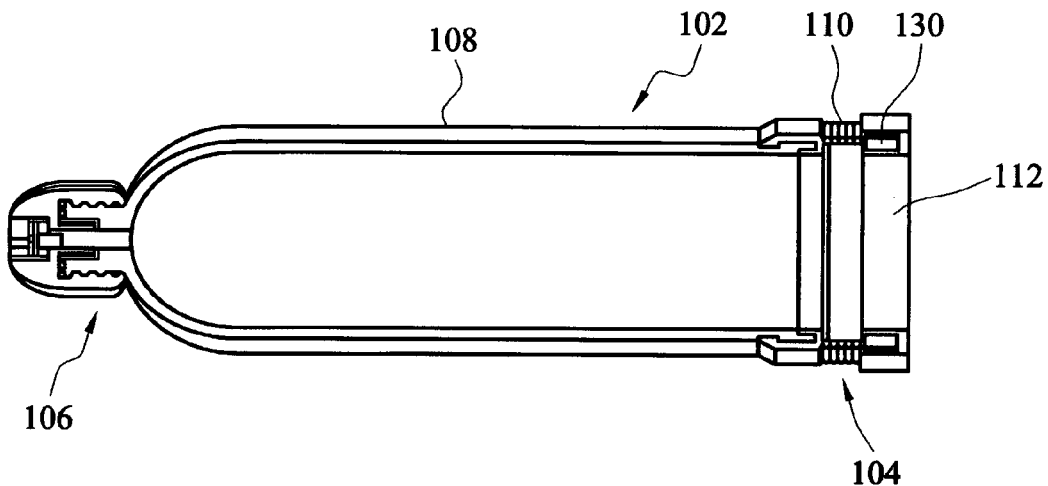
FIG. 2 shows a sectional view of the pump in a semi-compressed configuration.
Figure 3:
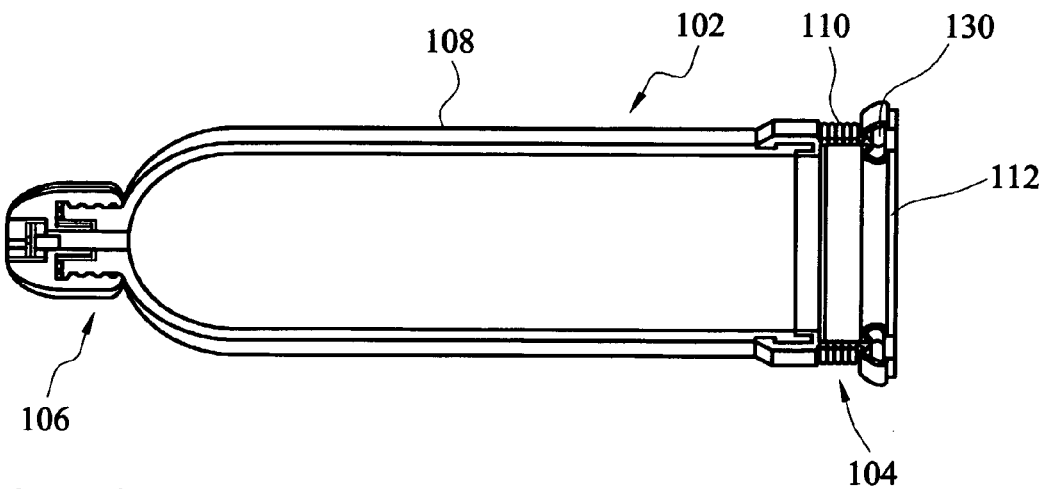
FIG. 3 shows a sectional view of the pump in a fully compressed configuration.

Referring to FIGS. 1, 2 and 3 there is shown a pump 102 having a cylindrical chamber 108 which is generally hollow, a base section 104 at a first end thereof and a head section 106 at a second end thereof.

Figure 6:
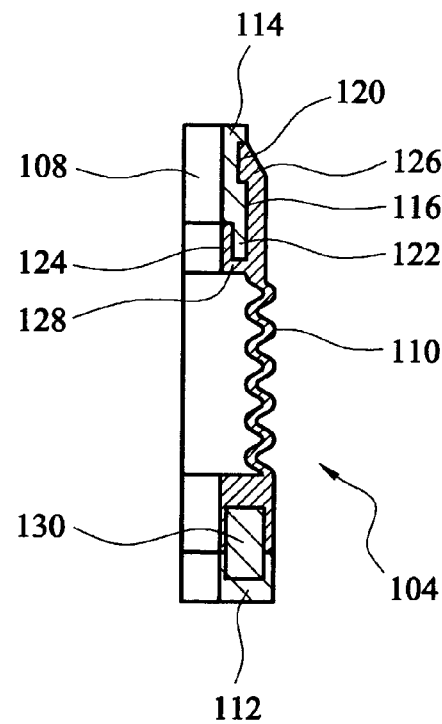
FIG. 6 shows an enlarged sectional view of a base section of the pump.

The base section 104 is shown enlarged in FIG. 6 and has a rubber gaiter 110 which connects at an upper end thereof to an exterior face 116 of a fixing ring 114 which is formed of polycarbonate. The fixing ring 114 is attached onto the first end of the hollow chamber 108 by its interior face 116. The exterior face 116 of the fixing ring 114 has a recess section 120 toward an upper edge thereof and an overhanging rim 122 toward a lower edge thereof. The rim 122 is laterally spaced from the hollow chamber 108 and thus forms a circumferential aperture 124 between the rim 122 and the hollow chamber 108.

The upper edge of the gaiter 110 is shaped to correspond with the exterior face 116 of the fixing ring 114. Thus the gaiter 110 has a protrusion 126 around its upper edge which is accepted within the recess section 120 of the fixing ring 114. Furthermore, the gaiter 110 also has a lip 128 which is accepted into the circumferential aperture 124 between the rim 122 and the hollow chamber 108. In this manner the gaiter 110 is offered greater lateral support with regard to the hollow chamber 108.

At a lower end of the rubber gaiter 110 there is attached a sealing ring 112 which is formed from closed cell rubber sponge. Within the sealing ring 112, is a circumferential chamber 130. The chamber 130 is hollow and is filled with a gas, such as, for example air.

In use, the gaiter may be compressed in a concertina type action, thus decreasing the volume inside the pump. The gaiter 110 has spring properties which restore its compressed state back to its uncompressed state. A further decrease in volume within the pump can be achieved by compression of the gas filled chamber 130.

Figure 4:
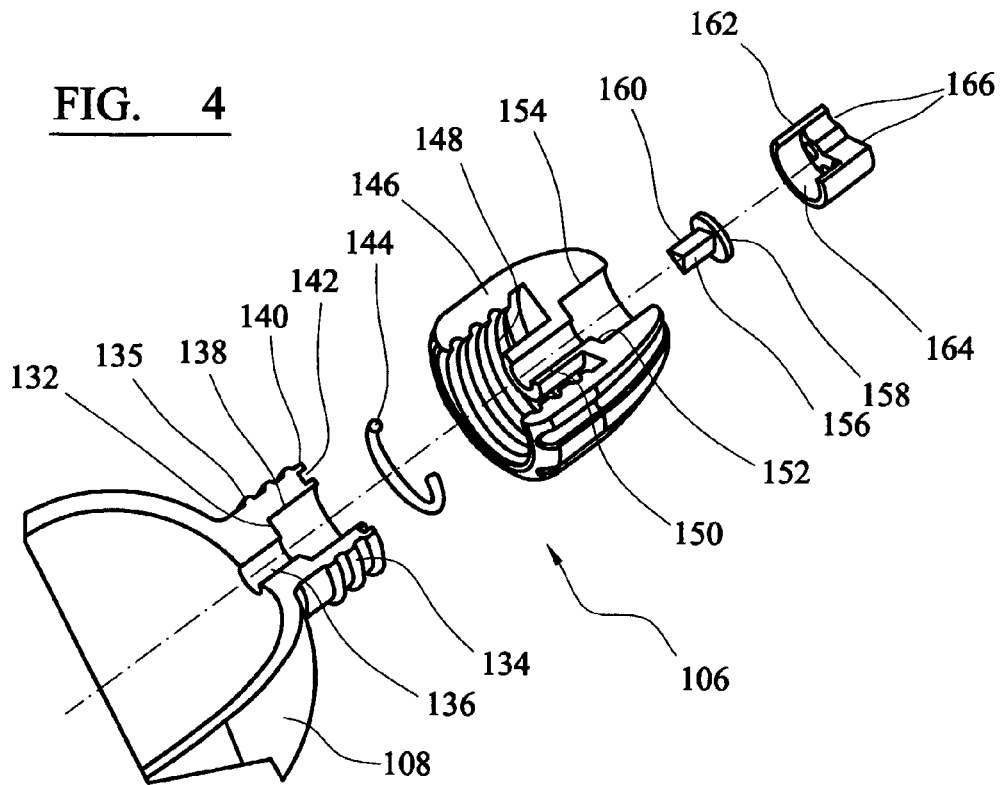
FIG. 4 shows an exploded view of a head section of the pump.
Figure 5:
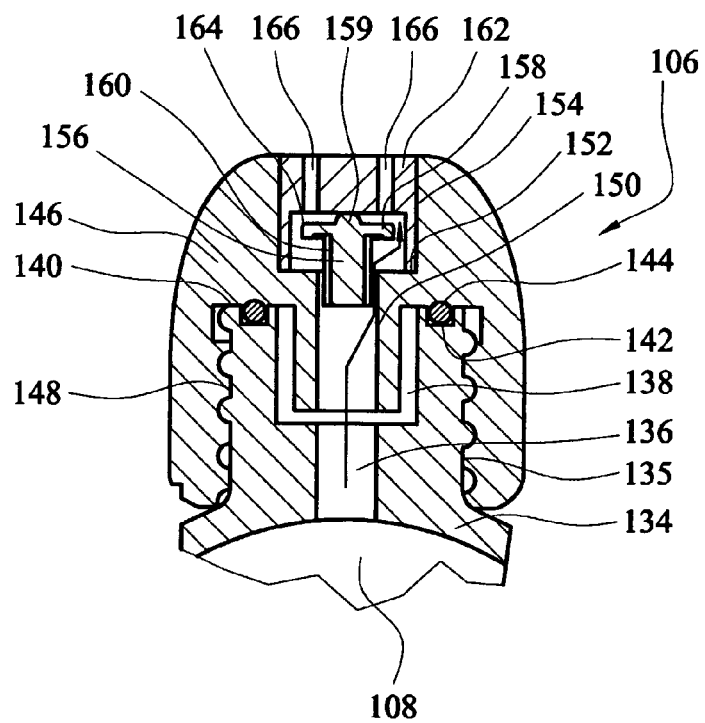
FIG. 5 shows an enlarged sectional view of the head section of the pump.

The head section 106 is shown enlarged in FIGS. 4 and 5. The hollow chamber 108 narrows toward a second end thereof to a neck section 134. The neck section 134 is circular in cross section and has an external threaded portion 135 around its circumference. The neck section 134 is substantially concentric with the hollow chamber 108 and has a two stage outlet centrally disposed therein. The first stage of the outlet 136, which is circular in cross section, extends from a lower end to approximately half way up the neck section 134 to a shoulder section 132. The second stage of the outlet 138 extends from the shoulder section 132 to an upper edge of the neck section 134. The outlet radially expands at the shoulder section 132 such that the second, upper, stage of the outlet 138 is circular in cross section, concentric with the first, lower, stage 136, but radially larger.

The upper face 140 of the neck section is annular and has a circumferential groove 142 thereon. When the head section is fully assembled as shown in FIG. 5, a rubber O-ring 144 is located within the groove 142.

The head section 106 further comprises a cap section 146 which has an internal thread 148 which is of an appropriate size to engage with the external thread 135 of the neck section 134. In a similar manner to the two stage neck outlet, the cap section 146 has a further two stage outlet. The first stage 150 of the cap outlet extends from a lower region of the cap to a valve seat 152. The second stage 154 of the cap outlet extends from the valve seat to an upper end of the cap section 146. Both stages of the cap outlet 150, 154 are substantially concentric with the hollow chamber 108 and circular in cross section. However, the second stage 154 of the cap outlet is radially larger than the first stage 150.

The cap section 146 further comprises a valve 156 having a disc section 158 and a shaft section 160 extending perpendicularly away from the radial centre of a lower face of the disc section 158. On an upper face of the disc section 158 there is a centrally disposed dome shaped protrusion 159. The lower face of the disc section 158 has an annular lip 160 toward an outer edge thereof to improve the seal offered by the valve 156. When the head section is assembled, the shaft section 160 of the valve 156 extends into the first stage 150 of the cap outlet while the annular lip 160 of the lower face of the disc section 158 abuts the valve seat 152.

The cap section 146 further comprises a plug 162 which has a lower outlet region 164 and a number of small upper outlet regions 166. The lower outlet region 164 is circular in cross section and concentric with the hollow chamber 108. The upper outlet regions 166, of which there are five, are circular in cross section and are arranged roughly in a pentagon around a central point which is concentric with the hollow chamber 108. When the cap section 146 is assembled, the plug 162 sits in the second stage 154 of the cap outlet. A chamber is formed between the second stage outlet 154 of the cap and the first stage outlet 164 of the plug in which the valve 156 is housed.

As shown in FIG. 5, the head section is assembled by screwing the cap section 146 onto the neck section 134, the lower stage 150 of the cap outlet being accommodated within the upper stage 138 of the neck outlet. When assembled, the head section 106 forms a non-return valve between the interior and exterior of the hollow chamber 108. When fluid pressures between the inside and outside of the pump are different, this pressure may not be equalized by flowing over the side of the neck section 134 and down the threaded section (or vice versa) because of the seal between the neck section 134 and the cap section 146 caused by the O-ring 144.

Therefore, in order for fluid to escape from the hollow chamber 108, the fluid must pass through the lower stage 136 of the neck outlet, through the lower stage 150 of the cap outlet, displace the valve 156 upward from the valve seat 152 (note that the valve cannot be displaced so as to abut the underside of the upper outlet regions 166 of the plug 162 because of the centrally disposed dome shaped protrusion 159 on an upper face of the disc section 158 of the valve 156). The fluid then passes through the second stage of the cap outlet and finally through the outlet regions of the plug 162. Fluid is prevented from flowing back into the hollow chamber 108 through the valve because pressure from outside the chamber 108 forces the disc section 158 of the valve to abut the valve seat 152 more firmly, thus not allowing fluid to enter.

In order to equalize the pressure between the inside and outside of the pump 102, the cap section 146 must be unscrewed from the neck section 134 so as to release the seal caused by the O-ring 144 so that fluid may flow over the threaded section, through the neck outlet and into the chamber 108.

In order to use the pump to produce an erection to a human penis, the pump 102 and a user should be immersed in liquid, such as in a bath, hot tub or jacuzzi. The flaccid or semi erect penis is then placed into the hollow chamber 108 via the base section 104. The sealing ring 112 is pulled down so that it abuts the user's pubic area and forms a seal. The cap section 146 is firmly screwed onto the neck section 134 such that a seal is formed by the O-ring 144 as described above. The user then pulls the pump toward the body thus causing the gaiter 110 to compress as shown in FIG. 2. Fluid within the chamber is thereby expelled through the non-return valve of the head section 106, because the volume of the chamber 108 is decreased. The spring return force of the gaiter 110 attempts to restore the pump to its original internal volume and thereby reduces the pressure inside the chamber 108. The gaiter 110 is once more compressed to expel more liquid through the non-return valve of the head section 106. Now, because the liquid within the chamber is substantially inexpandable, the spring return force of the gaiter 110 is unable to return the gaiter 110 to its uncompressed state. The penis is now forced to expand (by the ingress of blood) in order to return the gaiter 110 to its uncompressed state.

When the gaiter 110 is fully compressed, the pump may be pulled into the body further thus compressing the gas filled chamber 130 and slightly reducing further the volume within the pump 102 as shown in FIG. 3. In this manner a second stage pump, ejecting tiny volumes of fluid from the chamber 108 may be used. The spring return force of the hollow chamber 130 is greater than that of the gaiter 110. Therefore, as the penis expands, the gas filled chamber 130 will return to its uncompressed state first, before the gaiter 110 starts to uncompress.

In use, a user may use the second stage pump by compressing the gas filled chamber 130 and when it returns to its uncompressed state (because of an increase in size of the penis) recompress the gas filled chamber 130.

When the penis is fully erect (after perhaps 20 minutes) the pressure on the penis may be released be unscrewing the cap section 146 from the neck section 134 thereby breaking the seal of the O-ring 144.

Figure 7:
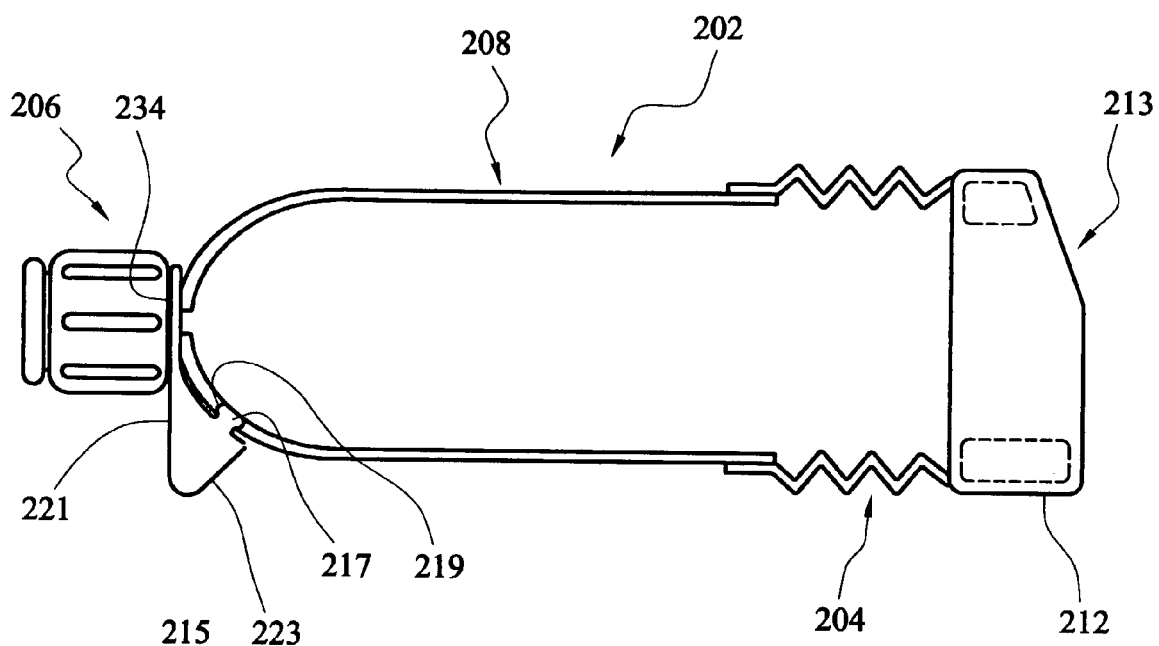
FIG. 7 shows a sectional view of a second embodiment of the pump.

Referring to FIG. 7 there is shown a second embodiment of the pump 202 having a chamber 208, a base section 204 and a head section 206 which generally correspond to the chamber 108, the base section 104 and the head section 106 of the first embodiment of the pump 102.

The differences between the second embodiment of the pump 202 and the first embodiment 102 are as follows. The sealing ring 212 of the pump 202 has a wedge shaped cut away section 213 to allow it to fit more comfortably on the body of a user. Particularly, the wedge shaped cut away section 213 is positioned over the testicles of a user thus preventing excess pressure being applied thereto in order to obtain a seal between the pump 202 and the body of a user.

Figure 8:
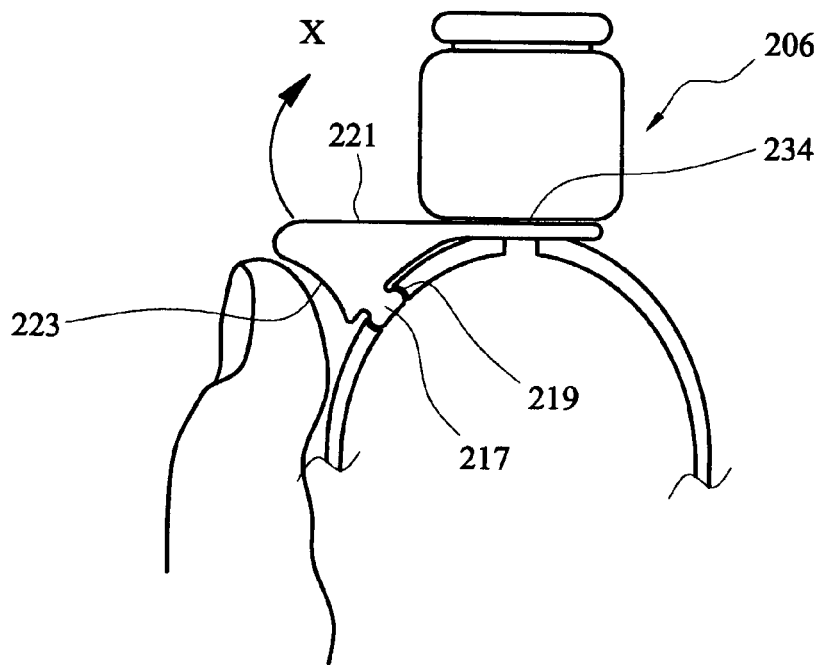
FIG. 8 shows an enlarged view of a head section of the pump of the second embodiment.

A further difference is the addition of a pressure release button 215 which comprises a plug 217 which extends into an aperture 219 in a wall of the chamber 208. The plug 217 extends from an underside of a collar 221 which is situated around a neck 234 of the head section 206. The collar 221 extends radially further than the walls of the chamber 208 and thus has a ledge 223 on its underside which (referring now also to FIG. 8) may be urged upward (as shown by arrow "X") by a user, thus removing the plug 217 from the aperture 219.

The plug 217 and aperture 219 are situated at a position toward the head section 206 and generally opposite the wedge shaped cut away section 213. In this manner, in use, the plug 217 and aperture 219 should face a user's torso. This relative positioning of the plug 217 and aperture to the cut away section 213 serves to position the pump 202 correctly for use.

In use, a user may release the pressure within the chamber by manually operating the pressure release button 215 thus removing the plug 217 from the aperture 219. This serves as an added safety feature of the pump 202.

Otherwise, the pump 202 works in the same way and contains the same advantages on the pump 102.

A pump made in accordance with the present invention has the advantage that the fluid within the chamber (being liquid) cannot expand, thus the penis is forced to expand due to the spring return force of the gaiter 110 and the gas filled chamber 130. If the chamber 108 were gas filled, then the air could simply expand thus encouraging the penis to expand, but not forcing it.

A further advantage is the provision of a second stage pump to regulate the ejection of tiny amount of fluid from the chamber 108 thus allowing the user to fine tune the pressure applied to the penis.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A pump comprising a chamber adapted to receive a penis, a non-return valve, pumping means operable to pump fluid from the chamber, and sealing means operable to seal the pump onto the body of a user, the sealing means comprising a cut away section on a face thereof, which seals against the body of a user, when in use.

2. A pump according to claim 1, wherein the chamber is substantially circular in section.

3. A pump according to claim 1, wherein the chamber is transparent.

4. A pump according to claim 1, wherein the chamber comprises a neck section toward a second end thereof, which comprises an outlet.

5. A pump according to claim 1, wherein the pump comprises a cap section within which is accommodated the non-return valve.

6. A pump according to claim 4, wherein the cap section is adapted to fit over the neck section and form a fluid tight seal therewith.

7. A pump according to claim 1, wherein the pump is a penis pump.

8. A pump according to claim 5, wherein the non return valve is adapted to allow the expulsion of fluid from the chamber, but not the ingress of fluid into the chamber.

9. A pump according to claim 5, wherein sealing means are provided between the cap section and the neck section.

10. A pump according to claim 5, wherein the cap section is adapted to be screwed onto the neck section.

11. A pump according to claim 1, wherein the pumping means is situated toward a first end of the chamber.

12. A pump according to claim 1, wherein the pumping means is manually actuated.

13. A pump according to claim 1, wherein the pumping means extends from a first end of the chamber.

14. A pump according to claim 1, wherein the pumping means comprises a compressible gaiter.

15. A pump according to claim 1, wherein the pumping means comprises a resilient bias operable to return the pumping means to an uncompressed configuration.

16. A pump according to claim 1, wherein the sealing means is situated at a first end of the pump.

17. A pump according to claim 1, wherein the sealing means comprises a sealing ring which is made from closed cell rubber sponge or similar.

18. A pump according to claim 1 which further comprises pressure release means.

19. A pump according to claim 18, wherein the pressure release means comprise a plug which is accommodated in an aperture in a wall of the chamber.

20. A pump according to claim 1, wherein, the pumping means further comprises a gas filled chamber.

21. A pump according to claim 20, wherein the gas filled chamber is annular in shape.

22. A pump according to claim 20, wherein the gas filled chamber is attached to an inner face of the sealing ring.

23. A pump according to claim 20, wherein the gas filled chamber is operable to be compressed by the application of pressure by a user.

24. A pump according to claim 20, wherein a spring return force of the gas filled chamber is greater than the resilient bias of the gaiter.

25. A method of causing or enhancing an erection of a human penis comprising immersing a pump as defined by claim 1 in water, placing a flaccid penis into a chamber of the pump and using pumping means to pump water from the chamber through a non-return valve.

* * * * *